United States Patent [19]
Duff et al.

[11] Patent Number: 5,898,094
[45] Date of Patent: Apr. 27, 1999

[54] TRANSGENIC MICE EXPRESSING APPK670N,M671L AND A MUTANT PRESENILIN TRANSGENES

[75] Inventors: Karen Duff, Tampa; John Hardy, St. Augustine, both of Fla.

[73] Assignee: University of South Florida, Tampa, Fla.

[21] Appl. No.: 08/903,518

[22] Filed: Jul. 30, 1997

Related U.S. Application Data

[60] Provisional application No. 60/028,937, Oct. 21, 1996, and provisional application No. 60/029,711, Nov. 12, 1996.

[51] Int. Cl.$^6$ .............................. C12N 15/00; C12N 5/00; A61K 49/00
[52] U.S. Cl. .................... 800/2; 800/DIG. 1; 435/172.3; 424/9.2
[58] Field of Search ................................. 800/2, DIG. 1; 435/172.3; 424/9.2

[56] References Cited

U.S. PATENT DOCUMENTS

| | | | |
|---|---|---|---|
| 4,736,866 | 4/1988 | Leder et al. | 800/1 |
| 4,873,191 | 10/1989 | Wagner et al. | 435/435 |
| 5,151,508 | 9/1992 | Salbaum et al. | 536/435 |
| 5,175,383 | 12/1992 | Leder et al. | 800/2 |
| 5,175,384 | 12/1992 | Krimpenfort et al. | 800/2 |
| 5,221,778 | 6/1993 | Bryre et al. | 800/2 |
| 5,288,846 | 2/1994 | Quertermous et al. | 435/435 |
| 5,298,422 | 3/1994 | Schwartz et al. | 435/435 |
| 5,347,075 | 9/1994 | Sorge | 800/800 |
| 5,387,742 | 2/1995 | Cordell | 800/424 |
| 5,464,764 | 11/1995 | Capecchi et al. | 435/435 |
| 5,525,714 | 6/1996 | Van Broeckhoven et al. | 536/536 |
| 5,602,299 | 2/1997 | Lazzarini | 800/800 |
| 5,604,131 | 12/1997 | Wadsworth et al. | 435/536 |
| 5,612,486 | 3/1997 | McConlogue et al. | 800/2 |

FOREIGN PATENT DOCUMENTS

| | | | |
|---|---|---|---|
| 9451700 | 4/1991 | European Pat. Off. | C12N 15/00 |
| 9653154 | 7/1994 | European Pat. Off. | A01K 67/027 |
| 9206187 | 4/1992 | WIPO | C12N 15/00 |
| 9211358 | 7/1992 | WIPO | C12N 15/00 |
| 9213069 | 8/1992 | WIPO | C12N 15/00 |
| 9302189 | 2/1993 | WIPO | C12N 15/00 |
| 9314200 | 7/1993 | WIPO | C12N 15/00 |
| 9406908 | 3/1994 | WIPO | C12N 15/00 |
| 9412627 | 6/1994 | WIPO | C12N 15/00 |
| 9224266 | 10/1994 | WIPO | C12N 5/00 |
| 9423049 | 10/1994 | WIPO | C12N 15/87 |
| 9228123 | 12/1994 | WIPO | C12N 15/00 |
| 9606927 | 3/1996 | WIPO | C12N 5/00 |

OTHER PUBLICATIONS

Ali et al., 1996. Artificial Strain–Specific Signs of Incipient Brain Amyloidosis in APP Transgenic Mice. Neur. of Aging, 17(2):223–234.

Andra et al., 1996, "Expression of APP in Transgenic Mice: A Comparison of Neuron–Specific Promoters", Neur. of Aging, 17(2)P183–P190.

Borchelt et al., 1996, "Familial Alzheimer's Disease–Linked Presenilin 1 Variants Elevate A–β–1–42/1–40 Ratio in Vitro and in Vivo", Neuron, 17:1005–1013.

Burke and Olson, 1991. "Preparation of Clone Libraries in Yeast Artificial–Chromosome Vectors" in Meth. in Enzymology, vol. 194, Academic Press, Inc., Chap. 17, pp. 251–270.

Cai et al., 1993, "Release of Excess Amyloid β Protein from a Mutant Amyloid β Protein Precursor", Science, 259:514–516.

Capecchi, 1989, "Altering the genome by homologous recombination" Science, 244:1288–1292.

Citron et al., 1992, "Mutation of the β–amyloid precursor protein in familial Alzheimer's disease increases β–protein production", Nature 360:672.

Cruts et al., 1996, "The Presenilin Genes: A New Gene Family Involved in Alzheimer Disease Pathology", Human Molecular Genetics, 5 (Review):1449–1455.

Davies et al., 1992, "Targeted alterations in yeast artificial chromosomes for inter–species gene transfer", Nucleic Acids Research, 20(11):2693–2698.

Dickinson et al., 1993, "High frequency gene targeting using insertional vectors", Human Molecular Genet., 2(8):1299–1302.

Duff et al., 1996, "Increased amyloid–β42(43) in brains of mice expressing mutant presenilin 1", Nature, 383:710–713.

Duff and Lincoln, 1995. "Insertion of pathogenic mutation into yeast artificial chromosome containing human APP gene and expression in ES cells", Res. Adv. in Alzheimer's Disease.

Games et al., 1995, "Alzheimer–type neuropathology in transgenic mice overexpressing V717F. β–amyloid precursor protein", Nature, 373:523–527.

Goate et al., 1991, "Segregation of a missense mutation in the amyloid precursor protein gene with familial Alzheimer's disease", Nature 349:704–706.

Gordon, 1989, "Transgenic Animals", Intl. Rev. Cytol, 115:171–229.

(List continued on next page.)

*Primary Examiner*—Deborah Crouch
*Attorney, Agent, or Firm*—Kohn & Associates

[57] ABSTRACT

A method of preparing a transgenic animal model with enhanced, accelerated pathology for Alzheimer's Disease (AD) and the transgenic animal made by the method is disclosed. The method includes producing an $F_1$ generation by crossing a first and second transgenic parent each carrying a different expressible transgene for differing aspects of the same desired phenotype associated with AD pathology. The offspring of the $F_1$ generation are then screened and those which carry a transgene from each parental transgenic animal resulting in an enhanced pathology for Alzheimer's Disease are selected. In a preferred embodiment the AD-associated pathology is for amyloid accumulation. In an embodiment a mutant presenilin transgene and a transgene for a mutant amyloid precursor protein are used. In a further embodiment the mutant presenilin transgene is the PS1 M146L mutation and the mutant amyloid precursor protein transgene is the Swedish mutation (APP695 isoform containing a K670N,M671L mutation (APP770 numbering)).

14 Claims, 1 Drawing Sheet

OTHER PUBLICATIONS

Hsiao et al., 1996, "Correlative Memory Deficits, A–β Elevation and Amyloid Plaques in Transgenic Mice", Science, 274:99–102.

Hsiao et al., 1995, "Age–Related CNS Disorder and Early Death in Transgenic FVB/N Mice Overexpressing Alzheimer Amyloid Precursor Proteins", Neuron, 15:1203–1218.

Huxley et al., 1991, "The human HPRT gene on a yeast artificial chromosome is functional when transferred to mouse cells by cell fusion", Genomics, 9:742–750.

Jakobovits et al., 1993, "Germ–line transmission and expression of a human–derived yeast artificial chromosome", Nature, 362:255–261.

Jarrett et al., 1993, "Carboxy Terminus of β–Amyloid Protein is Critical for Seeding of Amyuloid Formation . . . ", Biochemistry, 32:4693–4697.

Lalonde and Thifault, 1994, "Absence of an Association Between Motor Coordination and Spatial Orientation in Lurcher Mutant Mice", Behavior, 24:497–501.

Lamb et al., 1993. "Introduction and expression of the 400 kilobase precursor amyloid protein gene in transgenic mice", Nature Genetics, 5:22–29.

Lavitrano et al, 1989, "Sperm Cells as Vectors for Introducing Foreign DNA into Eggs: Genetic Transformation of Mice" Cell 57:717–723.

Levy–Lahad et al., 1995, "Candidate Gene for Chromosome 1 Familial Alzheimer's Disease Locus", Science, 269:973–977.

L'Hernault and Arduengo, 1992, "Mutation of Putative Sperm Membrane Protein in *Caenorhabditis elegans* Prevents Sperm Differentiation",.J. Cell Biology, 119(1):55–68.

Lo, 1983, "Transformation by Iontophoretic Microinjection of DNA Multiple Integrations Without Tandem Insertions", Mol. Cell. Biol 3(10):1803–1814.

Loring et al., 1996, "Rational Design of Animal Model for Alzheimer's Disease: Intro. of Mult. Human Genomic Transgenes . . . ", *Neur. of Aging,* 17(2):173–182.

Mann et al., 1996, "Amyloid β Protein Deposition in Chrom. 14–linked Alzheimer's Disease", Annals Neurol, 40:149–156.

Malherbe et al., 1996, "Lack of β–Amyloidosis in Transgenic Mice Expressing Low Levels of Aamilial Alzheimer's Disease Missence Mutations", 17(2): 205–214.

Mucke et al., 1994, "Synaptotrophic effects of human amyloid β protein precursors in cortex of transgenic mice", Brain Res., 666:151–167.

Neve et al., 1996, "Transgenic Mice expressing APP–C100 in the Brain", Neuro. of Aging, 17(2):191–203.

Pearson and Choi, 1993, "Expression of the human b–amyloid precursor protein gene from a yeast artificial chromosome in transgenic mice". Proc. Natl. Scad. Sci. USA, 90:10578–10582.

Reaume et al., 1996, Enhanced amyuloidogenic processing of the β–amyloid precursor protein in gene–targeted mice . . . , J. Biol. Chem. 271(38):23380–23388.

Rothstein, 1991, "Targeting, disruption, replacement, and allele rescue: integrative DNA transformation in yeast" in Meth. in Enzymology, (Academic Press) Chap. 19, 194:281–301.

Schedl et al., 1993, "A yeast artificial chromosome covering the tyrosinase gene confers copy number–dependent expression in transgenic mice", Nature, vol. 362:258–261.

Scheuner et al., 1996, "Secreted amyloid b–protein similar to that in senile plaques of AD is increased in vivo by presenilin 1 and 2 . . . ", Nature Med., 2(8):864–870.

Sherrington et al., 1996, "Cloning of a gene bearing missense mutations in early–onset familial Alzheimer's disease", Nature, 375:754–760.

Strauss et al., 1993, "Germ line transmission of a yeast artificial chromosome spanning the murine $a_1$ (I) collagen locus", Science, 259:1904–1907.

Suzuki et al., 1994, "Increased Percentage of Long Amyloid β Protein Secreted by Familial Amyloid β Protein Precursor ($\beta APP_{717}$) Mutants", Science, 264:1336–1340.

Thompson et al, 1989, "Germ Line Transmission and Expression of a Corrected HPRT Gene Produced by Gene Targeting in Embryonic Stem Cells", Cell 56:313–321.

Van der Putten et al, 1985, "Efficient insertion of genes into the mouse germ line via retroviral vectors", PNAS USA 82:6148–6152.

Duff, 1994, "Modeling Alzheimer's Disease in Transgenic Mice", J Florida M.A. 91(9):625–628.

Felsenstein et al (1995) Alzheimer's Parkinson's Diseases, L. Hanin et al, ed., Plenum Press, New York, pp. 401–409.

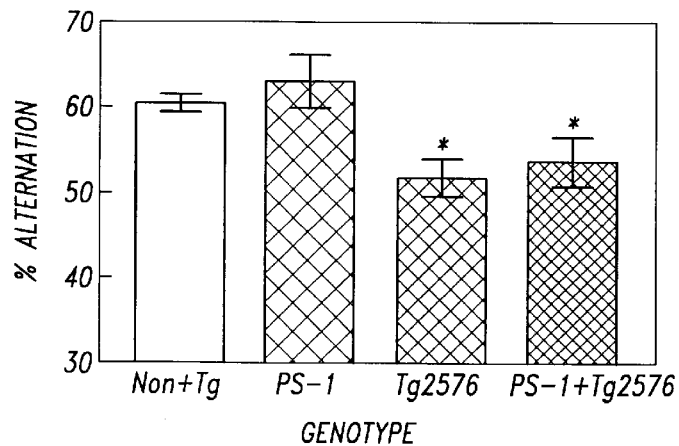
*Fig—1A*
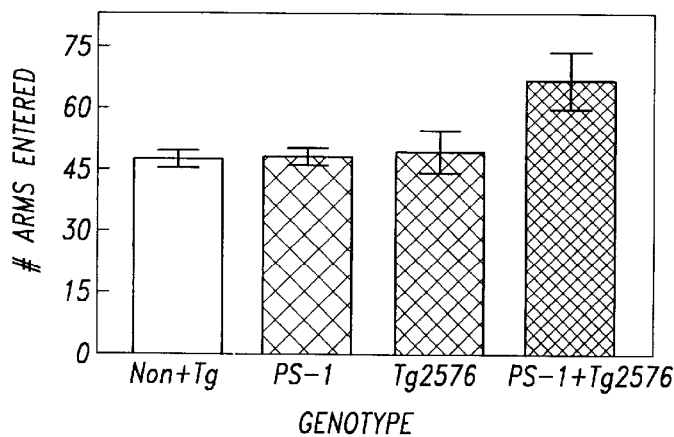
*Fig—1B*
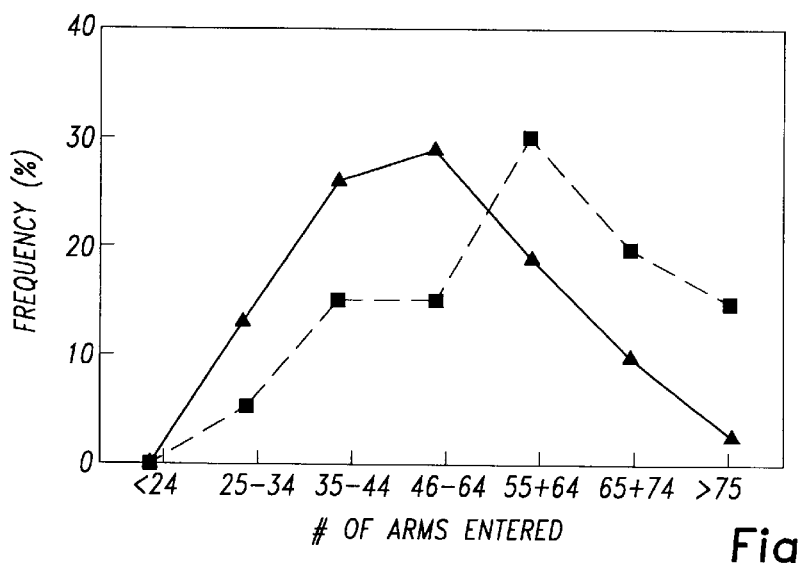
*Fig—1C*

TRANSGENIC MICE EXPRESSING APPK670N,M671L AND A MUTANT PRESENILIN TRANSGENES

This application claims priority from U.S. Ser. No. 60/028,937, filed Oct. 21, 1996 and from U.S. Ser. No. 60/029,711, filed Nov. 12, 1996.

FIELD OF THE INVENTION

The present invention relates to the production and use of transgenic animal models including methods of modulating the phenotype resulting from expression of the integrated transgenes. More particularly, the invention relates to improving models of neurodegerative disorders including models for Alzheimer's Disease and the animals produced therefrom.

BACKGROUND OF THE INVENTION

Transgenic animals are being utilized as model systems for studying both normal and disease processes. In general an exogenous gene with or without a mutation is transferred to the animal host system and the phenotype resulting from the transferred gene is observed. Other genetic manipulations can be undertaken in the vector or host system to improve the gene expression leading to the observed phenotype (phenotypic expression). The gene may be transferred under the control of different inducible or constituent promoters, may be overexpressed, the endogenous homologous gene may be rendered unexpressible and the like. [PCT Application WO 92/11358; U.S. Pat. No. 5,221,778] However, even with these manipulations the desired phenotype is not always expressed (for example, see herein below regarding PS transgenes). Further, as set forth in U.S. Pat. Nos. 5,602,299 and 5,221,778 various breeding programs to change the background, insert additional transactivator transgene, make the transgene homozygous or have hosts carrying two copies of the transgene but inserted at two different sites have been disclosed. However, again these methods do not always improve the phenotypic expression of the transgene such that the model system more closely resembles the desired phenotype. Therefore additional methods are needed to improve and/or modulate the phenotype of transgenic animals.

Transgenic model systems are needed to study neurodegenerative disorders, both to understand the underlying disease pathology as well as to test treatment protocols. Alzheimer's disease (AD) is a neurodegenerative disorder with a progressive dementia characterized by the presence of extracellular amyloid deposits (composed mainly of β-amyloid (Aβ)) and intraneuronal tangles, (consisting largely of the cytoskeletal protein tau), in specific brain regions. Its symptoms include gradual memory loss, declined ability to perform routine tasks such as eating, confusion, disorientation, the inability of the patient to care for him or herself, and eventually death. The American Health Assistance Foundation has reported that presently more than four million Americans are believed to have AD, and each year 100,000 Americans die because of AD and 250,000 new cases of AD are diagnosed. Moreover, one out of every ten Americans 65 years and older have AD and almost half of those 85 years and older have the disease.

Although AD in general is associated with patients in their late 60s, 70s and older, Familial Alzheimer's Disease (FAD) has been documented in patients in their thirties and forties. FAD is genetic autosomal dominant form of AD. Although the genetic causes of FAD are not thought to be the same as AD, the FAD phenotype appears to be pathologically similar to AD. It has been reported that 10% of all AD cases are FAD.

Autopsies of patients who suffered from FAD have shown the presence of neuritic plaques made up largely of beta-amyloid (Aβ) and neurofibrillary tangles consisting largely of deposits of tau protein [reviewed in Hardy and Duff, 1993]. Beta-amyloid is a 40–42 amino acid peptide produced by the proteolytic cleavage of the larger amyloid precursor protein (APP). APP is a transmembrane protein with a single transmembrane domain running from residue 700 to residue 722. The APP gene is located on chromosome 21 and contains 18 exons. APP isoforms resulting from alternative splicing form a set of polypeptides ranging from 563 to 770 residues in length. The beta amyloid fragment is encoded by the 3' half of exon 16 and the 5' half of exon 17, which also encodes APP's transmembrane domain. Most of the beta-amyloid cleaved from APP is forty (40) amino acid residues long and designated Aβ1-40.

Another form of beta-amyloid produced in much smaller amounts relative to the production of Aβ1-40 is a peptide 42–43 amino acid residues long. It is designated Aβ1-42 (43). This peptide is selectively deposited early in the FAD process. Experiments conducted in vitro have demonstrated this peptide forms insoluble aggregates much faster than Aβ1-40. Hence it is believed that increased production of Aβ1-42(43) occurs in patients genetically predisposed to FAD and initiates its pathology. Since both forms of beta-amyloid are insoluble, they deposit on neurons in the brain.

Genetic causes of AD include mutations in the APP gene on chromosome 21, the presenilin 1 (PS1) gene on chromosome 14 and the presenilin 2 (PS2) gene on chromosome 1 [Goate et al, 1991; Sherrington et al, 1995; Levy-Lahad et al, 1995]. All known mutations which cause AD have been shown to alter the processing of APP such that more amyloidogenic Aβ (Aβ42(43)) is generated. This had led to the hypothesis that aberrant APP processing and the generation of Aβ42(43) may underlie the early etiopathogenesis of FAD [Younkin, 1995; Scheuner, 1996; Cai et al, 1993; Citron et al, 1992; Suzuki et al, 1994].

In some patients suffering from FAD, a missense point mutation in exon 17 at a codon 717 (transcript 770) of the APP gene was determined responsible for the increased formation of beta-amyloid, and hence FAD [PCT Application PCT/GB92/00123]. Soon thereafter, other point mutations were found in the same codon in patients suffering from FAD [Hardy, 1993].

In an effort to develop animal models to study pharmaceutical agents designed to treat FAD, transgenic mice have been developed containing the missense point mutations of the human APP gene in their genome [Hsiao et al., 1996; Games et al., 1995; U.S. Pat. No. 5,612,486; PCT Applications WO 92/06187; WO 93/14200; WO 96/06927]. Since a mutated APP gene is expressed in their brains, these transgenic mice have the potential to serve as models for FAD. Models with overexpression of the APP gene. (with and without mutations) have also been developed [PCT Application WO 94/24266; WO 96/06927; European Patent Application EPO 653 154 A2].

Some of these APP gene transgenic mice have been shown to produce pathology which resembles that of FAD at one year of age and older [Hsiao et al., 1996 and Games et al., 1995]. The PDAPP mouse [Games, et al, 1995] expresses an APP minigene with the V717F mutation (Note mutations are abbreviated as the amino acid at location followed by the substituted amino acid). The Tg2576 mouse

[Hsiao et al, 1996] expresses the APP695 isoform containing a K670N,M671L mutation (APP770 numbering) which is often referred to as the Swedish mutation. In addition to AD-type pathology, Tg2576 shows cognitive impairment as measured by spontaneous alternation in a "Y" maze and spatial memory in a water maze suggesting that the manipulation of APP affects cognitive function in addition to pathology.

However, other APP gene transgenic mice do not produce or have weak FAD pathology. See Neve et al, 1996 for an example of weak pathology and Hsaio et al., 1995; Andra et al., 1996; Malherbe et al., 1996; Mucke et al., 1994 for examples of APP mice which do not show pathology and see Greenberg et al, 1996 for a review of additional APP gene transgenic mice which do not show pathology or show only weak pathology.

Analysis of the above suggests that these Alzheimer's models suffer from the limitation that they are unable to produce sufficient amounts of Aβ in the brain to initiate Alzheimer's related pathology. Therefore transgenic models producing sufficient amounts of Aβ in the brain in an accelerated manner and methods of making such transgenics are needed.

Recently, mutations in other genes, termed the Presenilin I (PSI) and Presenilin II (PS2) genes located on chromosomes 14 and 1, respectively, have also been shown to cause FAD. [Cruts, et al., 1996]. Research has demonstrated that peripheral cells from individuals with these presenilin mutations produce a greater amount Aβ1-42(43) than that produced in individuals having a non-mutant PS gene [Scheuner et al., 1996]. It has been suggested that the mode of pathogenesis produced by these mutated presenilin genes involves the production of more Aβ1-42(43) relative to the amount produced by a nonmutant (wildtype) PS1 or PS2 gene. Presently, the mechanism which causes this increased production of Aβ1-42(43) is not known.

Transgenic mice carrying mutations in PS1 do not appear to develop AD-type pathology but do show an elevation of Aβ42(43) [see Example herein]. This form of Aβ is highly amyloidogenic and forms the early core of amyloid deposits in AD brain [Mann et al, 1996; Jarrett et al, 1993]. Both PS1 and PS2 are known to influence APP processing [Scheuner et al, 1996 and see Example herein]. Sequence homology between the presenilins and a *C. elegans* protein involved in protein trafficking (SPE4) suggests that the presenilins may direct the compartmentalization and trafficking of APP [L'Hemault and Arduengo, 1992] and that mutant presenilins may direct APP along a pathway that results in elevated levels of Aβ42(43). In this way the biosynthetic pathways can be considered to be interactive.

The above transgenic animals provide the current models of Alzheimer's Disease. However, as discussed herein above many of these models are incomplete, in that the full pathology seen in humans is not seen, or as seen in the PS models, no pathology just elevated levels of Aβ1-42(43) are seen. Further, the models generally require that the mice age and the pathology is not seen until nine months and generally later [Hsaio et al., 1996]. This means that the animals must be maintained for extended periods of time. The cost of maintenance makes it difficult for many investigators to use these models.

It would be useful therefore to have transgenic models which show the full range of pathology of AD at an earlier age or a selected aspect of the pathology or for that matter any other human genetically based condition. The method should allow the modulation of the phenotype resulting from the expression of the transgenes. It would further be useful to have a model for AD in which the pathology onset is earlier (accelerated). Specifically, a model in which amyloid accumulation is enhanced and accelerated.

SUMMARY OF THE INVENTION AND ADVANTAGES

The present invention provides a method of preparing a transgenic animal model with enhanced, accelerated pathology for Alzheimer's Disease (AD) and the transgenic animal made by the method. The method includes producing an $F_1$ generation by crossing a first and second transgenic parent each carrying a different expressible transgene for differing aspects of the same desired phenotype associated with AD pathology. The offspring of the $F_1$ generation are then screened and those which carry a transgene from each parental transgenic animal resulting in an enhanced pathology for Alzheimer's Disease are selected.

In a preferred embodiment the AD-associated pathology is for amyloid accumulation. In an embodiment a mutant presenilin transgene and a transgene for a mutant amyloid precursor protein are used. In a further embodiment the mutant presenilin transgene is the PS1 M146L mutation and the mutant amyloid precursor protein transgene is the Swedish mutation (APP695 isoform containing a K670N,M671L mutation (APP770 numbering)).

The present invention also provides a method of modulating the phenotype of a transgenic animal model and the transgenic organism with the modulated phenotype. An $F_1$ generation is produced by crossing a first and second transgenic parent, each carrying a different expressible transgene at different steps in the same and/or interactive biosynthetic pathway for the desired phenotype of a transgenic animal. The offspring are screened and offspring selected in the $F_1$ generation which carry a transgene from each transgenic parent thereby providing a modulated phenotype.

The method of the present invention also provides a method of screening for two expressible transgenes which when expressed in the same animal result in a modulated phenotype. In this method an $F_1$ generation is produced by crossing a first and second transgenic parent each carrying a different expressible transgene at different steps in the same or an interactive biosynthetic pathways for the phenotype under consideration. Offspring are identified among the $F_1$ generation which carry a transgene from each transgenic parent and which result in a modulated phenotype. When offspring are identified with a modulated phenotype, a transgenic animal carrying the two expressible transgenes can be made.

DESCRIPTION OF THE DRAWINGS

Other advantages of the present invention will be readily appreciated as the same becomes better understood by reference to the following detailed description when considered in connection with the accompanying drawings wherein:

FIGS. 1A–C are graphs showing early behavioral changes in transgenic mice. Mice were tested for spontaneous alternation behavior in a symmetrical "Y" maze at 12–14 weeks. The alternation performance was decreased in the parent carrying the APP695 isoform containing a K670N,M671L mutation and doubly transgenic mice compared to M146L and non-transgenic litter mates (FIG. 1A). The activity of the mice in the "Y" maze was elevated in the doubly transgenic mice relative to all other genotypes (FIG. 1B). The frequency plot of "Y" maze activity measurements for each mouse indicates a right-shift in the frequency distribution (FIG. 1C). Doubly transgenic mice (dashed line; n=21) and the frequency distribution of the non-transgenic plus M146L mice (solid line; n=63) which had identical means and standard deviations (see FIG. 1B).

DETAILED DESCRIPTION OF THE PREFERRED EMBODIMENT

The present invention provides a method of producing a successor generation of transgenic animals with a modulated phenotype from that of the original/initial transgenic animals. The modulation can be either an enhancement of the original observed phenotype seen in the initial transgenic animals or a diminution of the phenotype. By modulation is meant that the characteristic phenotype shown by the transgene is more pronounced, appears earlier or later; where protein is produced more or less protein is produced than the parent strains or the like. Where earlier or accelerated, it is meant that the observed phenotype is seen at least one month earlier in the lifespan than the phenotype in the parental strain or similarly for later appearance.

For example, a modulated phenotype for a human disease model would show a pathology associated with the disease that more accurately reflects the human pathologic state including having more of the characteristics of the disease than the initial transgenic animal parental strains or the like. Alternatively, a modulated phenotype could reflect a faster or slower onset of the pathology of the human disease.

Specifically, the method produces an $F_1$ generation by crossing a first and second transgenic parent specifically selected to complement each other. By complement is meant that the transgenic parent carries a different expressible transgene at different steps/aspects in the same or interactive biosynthetic pathway for the phenotype or phenotype aspect that is to be modulated. In general the term aspect is used to describe a significant part/facet/feature of the phenotype that is being modulated. In general the term biosynthetic pathway is used as is known in the art. However, in producing a phenotype often the products of one biosynthetic pathway must interact with those of another to produce the observed phenotype and so the term can be used in a broader concept to include several specific biosynthetic pathways which interact to provide an observed phenotype.

In general where the transgene carries a mutation it is referred to by the mutation. The mutation is abbreviated by the non-mutant amino acid followed by the location in the sequence followed by the substituted amino acid.

The transgene generally is a human gene where a human condition is being studied. The transgene (generally in the form of cDNA) can be the nonmutant (often referred to as "wildtype") or a mutant human gene. Additionally, a non-mutant transgene can also be treated as is known in the art to express mutations.

The offspring of the $F_1$ generation with the modulated phenotype are utilized in animal models as for example testing of treatment modalities in a disease model or for pathogen susceptibility.

Further, one parent strain instead of carrying a direct human transgene may have the homologous endogenous gene modified by gene targeting such that it approximates the transgene. That is, the endogenous gene has been "humanized" and/or mutated [Reaume et al, 1996]. It should be noted that if the animal and human sequence are essentially homologous a "humanized" gene is not required. The transgenic parent can also carry an overexpressed sequence, either the nonmutant or a mutant sequence and humanized or not as required. The term transgene is therefore used to refer to all these possibilities.

Additionally, cells can be isolated from the offspring which carry a transgene from each transgenic parent and that are used to establish primary cell cultures or cell lines as is known in the art.

Where appropriate, a parent strain will be homozygous for the transgene. Additionally, where appropriate, the endogenous nontransgene in the genome that is homologous to the transgene will be nonexpressive. By nonexpressive is meant that the endogenous gene will not be expressed and that this nonexpression is heritable in the offspring. For example, the endogenous homologous gene could be "knocked-out" by methods known in the art. Alternatively, the parental strain that receives one of the transgenes could carry a mutation at the endogenous homologous gene rendering it nonexpressed.

The method of the present invention also provides a screening protocol to determine which combination of transgenes produce modulated phenotypes. These combinations can then be incorporated in a single transgenic animal to produce a modulated phenotype. That is, an engineered transgenic animal may be wanted that has incorporated in its genome two or more transgenes but that is not established by crossing rather is engineered by standard methods for making transgenic animals. For example, a transgenic organsim may be wanted wherein two or more transgenes are on the same vector under the control of the same promoter and which should have the required modulated phenotype. However due to the cost and effort of making the transgenic animal a screening is necessary to determine the most likely candidates to engineer.

In the screening method of the present invention an $F_1$ generation is produced by crossing a first and second transgenic parent each carrying a different expressible transgene at different steps/aspects in the same or interactive biosynthetic pathways for the phenotype or phenotype aspect under consideration. The offspring of the $F_1$ generation are tested and those offspring which carry a transgene from each transgenic parent are selected and observed for the modulated phenotype.

The transgenic parents are produced as is known in the art. The present invention provides for transgenic parental strains containing transgenes as described herein above and including gene targeted or overexpressed mutant or nonmutant transgenes and where appropriate as well as for knock-out strains carrying a transgene. Any method can be used which provides for stable, inheritable, expressible incorporation of the transgene within the nuclear DNA of an animal. These transgenic animals are constructed using standard methods known in the art and as set forth in U.S. Pat. Nos. 5,614,396 5,487,992, 5,464,764, 5,387,742, 5,347,075, 5,298,422, 5,288,846, 5,221,778, 5,175,384, 5,175,383, 4,873,191, 4,736,866 as well as Burke and Olson [1991], Capecchi [1989], Davies et al. [1992], Dickinson et al. [1993], Duff and Lincoln [1995], Huxley et al. [1991], Jakobovits et al. [1993], Lamb et al. [1993], Pearson and Choi [1993], Rothstein [1991], Schedl et al. [1993], Strauss et al. [1993]. Further, patent applications WO 94/23049, WO 93/14200, WO 94/06908, WO 94/28123 also provide information.

More specifically, any techniques known in the art may be used to introduce the transgene expressibly into animals to produce the parental lines of animals. Such techniques include, but are not limited to, pronuclear microinjection (U.S. Pat. No. 4,873,191); retrovirus mediated gene transfer into germ lines [Van der Putten et al., 1985]; gene targeting in embryonic stem cells [Thompson et al., 1989 and U.S. Pat. No. 5,614,396]; electroporation of embryos [Lo, 1983]; and sperm-mediated gene transfer [Lavitrano et al., 1989]. For a review of such techniques see Gordon [1989].

In an exemplar of the present invention as shown in the Example herein below a transgenic animal has been created for Alzheimer's Disease (AD) having a pronounced accelerated phenotype of an Aβ related phenotype of accumulated amyloid using the method of the present invention. The animal is a rodent and in a preferred embodiment, a mouse.

As discussed herein above the pathology of AD is related to aberrant amyloid production. Therefore in this transgenic model, genes relating to the biosynthetic pathways for the phenotype of amyloid accumulation have been used.

In a preferred embodiment for a model for AD the first parental animal carries an expressible transgene for a mutant presenilin transgene [Cruts et al., 1996; Duff et al., 1996] and the second parental animal carries an expressible transgene for a mutant amyloid precursor protein [U.S. Pat. Nos. 5,612,486; 5,602,299; 5,525,714; 5,604,131; 5,387,742; 5,151,508; PCT Patent Applications WO 93/14200; WO 96/06927; WO 94/12627; WO 93/02189; WO 92/06187; European Patent Applications EP 0 451 700 A1; EP 0 653 154 A2; Neve et al., 1996; Hsiao et al., 1996; Ali et al., 1996]. The APP gene can be a humanized targeted nonmutant sequence or mutant sequence and these can be overexpressed or not. Further overexpressed animal nonmutant or mutant sequences can also be used. The presenilin genes (PS1 and PS2) in the mouse and human have essentially homologous sequences so that targeted mutations can be used to generate the parent strain without the need to humanize first.

More specifically, the mutant presenilin transgene is M146L and the mutant amyloid precursor protein (APP) transgene is for an APP695 isoform containing a K670N, M671L mutation. However, any mutant presenilin or amyloid precursor protein gene or subsequently discovered homologs can be used that provide complementarity/interactivity for the expressed amyloid-associated AD phenotype of accumulation Aβ. In further embodiments overexpressed C terminal fragments of APP is used, or the PDAPP mouse [Games et al, 1995], and other APP mice [Sommer et al, 1996; Lamb et al, 1993; Reaume et al., 1996] can be used.

Utilizing the method of the present invention, $F_1$ progeny from a cross between a parental mouse carrying the mutant APP transgene for an APP695 isoform containing a K670N, M671L mutation (referred to herein as K670N,M671L) and a parental mouse carrying the mutant PS1 transgene for M146L were bred and examined in relation to histopathology and behavioral phenotype. In these animals, the expression of mutant PS1 in addition to the expression of mutant APP, accelerates the rate at which Aβ is deposited, most likely due to the PS1-mutant driven elevation in Aβ1-42(43). The double transgenic mice had accelerated formation of deposits containing Aβ (Table 1). Sections stained with the antibody 4G8 (which stains both human and mouse Aβ ending at either residue 40 or residue 42) labels numerous deposits in every doubly transgenic mouse killed between 26 and 32 weeks of age, generally at 29 weeks of age. Corresponding areas from littermate age-matched single transgenic K670N,M671L or M146L mice and non-transgenic littermates were negative for Aβ deposits. The positively staining Aβ deposits become apparent by 13 weeks of age and increased in number and size from that time point showing a modulated phenotype which accelerates the process of Aβ accumulation in the doubly transgenic mice.

All mice in these studies were subjected to a behavioral test battery at 12–14 weeks old. All groups of mice performed similarly on test of sensory and motor function. Body weights were similar for all genotypes. However, when mice were tested for spontaneous alternation behavior in the symmetrical "Y" maze, differences were observed in the total number of arm entries. This index of activity was modified by genotype. The doubly transgenic mice had increased activity compared with the K670N,M671L or M146L or non-transgenic littermates. Thus, as early as 12 weeks, there is a synergistic effect of PS1 and APP mutations on this behavioral measure.

These results clearly demonstrate that presenilin mutations accelerate development of the AD phenotype in K670N,M671L mice in a synergistic manner and provides a modulated phenotype. The data indicate that mutant presenilin affects the processing of mutant APP expressed from the K670N,MG71L transgene to enhance Aβ production, fibrillar plaque formation and affect behavior early in the life-spans of mice. The rapid development of the AD phenotype in these mice will be advantageous in addressing mechanistic issues of amyloid toxicity, and testing the efficacy of agents proposed to interact with select aspects of the AD phenotype.

The above discussion provides a factual basis for the method of developing transgenic animals which have a modified phenotype. The methods used with and the utility of the present invention can be shown by the following non-limiting examples and accompanying figures.

EXAMPLES

General Methods:

General methods in immunohistochemistry: Standard methods known in the art and not specifically described were generally followed as in Stites et al. (eds), Basic and Clinical Immunology (8th Edition), Appleton & Lange, Norwalk, Conn. (1994) and Johnstone & Thorpe, Immunochemistry in Practice, Blackwell Scientific Publications, Oxford, 1982.

General methods in molecular biology: Standard molecular biology techniques known in the art and not specifically described were generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989).

Genotyping Litters:

The resulting offspring were genotyped by cutting tail tips from weanlings, extracting DNA using a Promega genomic DNA extraction kit, transferring denatured DNA to nylon membrane and hybridizing duplicate samples with a DNA probe that recognizes either APP or PS1.

Sensory and Motor Function Tests: For all litters, mice were weighed between 12 and 14 weeks. The forelimb placing response of each mouse was checked by holding the mouse by the tail above a flat surface and slowly lowering the mouse to see if the forepaws reached outwards towards the surface. The righting reflex displayed when the mice were held with feet upwards and dropped from a height of 35 cm onto a soft surface of bedding, was used to test vestibular function. A loud metallic click to elicit the Preyer reflex (a backwards flick of the pinna) was used to test hearing. Testing for spontaneous seizures was accomplished by stressing each mouse by holding it by the tail for 30 seconds. Mice were then placed back in a cage and observed after a 30 minute interval for seizure activity. Motor coordination was investigated using the coat hanger test as described by Lalonde and Thifault (1994).

Behavioral Tests: Three month old mice were also tested for spontaneous alteration, using a protocol similar to those described by Hsiao [1996] and Maurice et al. [1996]. Mice were placed in the center of a symmetrical "Y" maze made of white acrylic and the sequence of arm entries over 8 minutes were recorded. Percentage alternation is the number of triads containing entries into all three arms (i.e. ABC, ACB, CAB, etc.) divided by maximum possible alternations (equivalent to the total number of arms entered minus 2)×100.

For statistical analysis, littermates of the same genotype were averaged, and the values for each litter were compared by ANOVA followed by Newman-Keuls to determine differences between individual groups (n=11–12 litters for each genotype; 33 non-transgenic, 30 M146L, 22 K670N,M671L and 20 doubly transgenic mice).

Immunohistochemical Protocols: Doubly transgenic (n=6), single transgenic K670N,M671L (n=5) and M146L (n=3) and non-transgenic mice (n=4; all 26–32 weeks old), and one 15 month old parental K670N,M671L mouse were sacrificed. One hemisphere of the brain was gently shaken in 0.9% saline for 30 minutes and immersion fixed in 4% paraformaldehyde for 24 hours, cryoprotected in 15% sucrose/PBS (2 hours) followed by an overnight immersion in 30% sucrose/PBS. Twenty five μm horizontal sections were prepared with a sliding microtome.

Immunohistochemistry was performed on floating sections using standard protocols. Primary antibodies recognizing Aβ residues 17–24 (4G8, Senetek, Maryland Heights, Mo., 1:1000) and GFAP (Boehringer Mannheim, Indianapolis, Ind., 1:1000) were used. GFAP stained sections were mounted on slides and counterstained with Congo red (Sigma Accustain Amyloid staining kit, St. Louis, Mo.). Congo red staining was evaluated using cross-polarized illumination. Only deposits that were green/red birefringement when the polarizer was rotated were counted as Congo red positive deposits. Additional sections were stained with 1% thioflavin S after 10 minutes in Mayer's hematoxylin to mask nuclear fluorescence. Counts of plaques were all made at 40× total magnification at each of 3 different dorsoventral planes.

Results

Progeny from a cross between parental mice carrying the APP695 isoform containing a K670N,M671L mutation (APP770 numbering) and parental mice carrying a mutant PS1 transgene M146L were examined in relation to histopathology and behavioral phenotype. In these animals, the expression of mutant PS1 in addition to the expression of mutant APP, accelerates the rate at which Aβ is deposited, most likely due to the PS1-mutant driven elevation in Aβ1-42 (43). All animals expressing the APP transgene show deficits in the behavioral test, spontaneous alternation, but this does not correlate with the deposition of Aβ suggesting that these deficits of cognitive impairment are not entirely related to a toxic component of visible amyloid deposits.

First litter progeny (19 animals) from the cross were sacrificed between 26 and 32 weeks of age. The histopathology from these animals shows that the double transgenic mice had accelerated formation of deposits containing Aβ relative to singly transgenic littermates. Sections stained with the antibody 4G8 (which stains both human and mouse Aβ ending at either residue 40 or residue 42) labels numerous deposits in every doubly transgenic mouse sacrificed between 26 and 32 weeks of age (6 mice, all three sections examined in each case). These deposits are also stained by Congo red when viewed under polarized light. Corresponding areas from age-matched K670N,M671L and M146L littermates and non-transgenic littermates were negative for Aβ deposits (see Table 1).

Thioflavin S positive deposits were only found in the double mutant mice cortex and hippocampus, with a slightly lower density in the more ventral regions of cortex. No deposits were observed in any other brain regions. Some of the deposits resemble a Maltese cross when stained with Congo red and viewed under cross-polarized light. Similar structures are seen in human AD brains. The number of thioflavin S deposits consistently exceeded the numbers found with Congo red or Aβ immunohistochemistry, but the values were highly correlated within the double mutant mice (r=0.93 for thioflavin S and Congo red and r=0.81 for thioflavin S and Aβ immunohistochemistry). These high correlation's suggest all three measurements reflect the same process of deposition, which varies slightly in each mouse. The higher absolute values for thioflavin S indicates the deposits are easier to identify with this technique.

The positive reaction of all three methods with the deposits in the doubly transgenic mice strongly indicates that they consist of fibrillar Aβ amyloid. As a control, a 15 month old parental K670N,M671L mouse was sacrificed and processed in parallel with the 26–32 week old mice. This mouse had deposits which were positively immunostained with Aβ, Congo red and thioflavin S.

Reactive astrocytes are seen surrounding the deposits when the slides are stained with a monoclonal antibody to glial fibrillary acidic protein (GFAP). The astrocytes appear in clusters within the cerebral cortex of the doubly transgenic mice. Few if any clusters of reactive astrocytes are present in 26–32 week old K670N,M671L mice, M146L littermates or non-transgenic littermates. Double-staining with Congo red revealed amyloid deposits in the center of these clusters of reactive astrocytes. Astrocytes clusters were present also in the hippocampus, but were not as discernible as in neocortex because of the higher basal GFAP content in this region of mouse brain. Similar clusters were apparent in the 15 month old parental K670N,M671L mouse.

Four younger doubly transgenic mice were sacrificed at 13 (n=2) or 15 (n=2) weeks of age. The 13 week old mice did not have Aβ deposits evaluated either by Aβ immunochemistry or Congo red staining. The 15 week old mice averaged one deposit per section, however, thioflavin S stained deposits were visible in both 13 and 15 week old doubly transgenic mice. Some of the thioflavin S deposits consisted of only a few thread-like profiles. The deposits were very small, and substantially fewer in number (less than 5 per section) than those in the 26–32 week old mice (average of 77 per section; Table 1). Thus, the Aβ deposits are becoming apparent by 13 weeks of age and increase in number and size from that time.

All mice in these studies were subjected to a sensory and motor function and behavioral test battery at 12–14 weeks old. All groups of mice performed similarly on tests of sensory and motor function including a wire hang test (strength and coordination), righting response (vestibular), Preyer's response (auditory) and the forelimb placing response (visual and motor). Body weights were similar for all genotypes.

However, when mice were tested for spontaneous alternation behavior in the symmetrical "Y" maze, differences were observed. Alternation performance was modified by genotype (FIG. 1A; ANOVA: $F(3,43)=5.64$, $p<0.005$). The percentage of alternations was significantly lower in both the doubly transgenic and K670N,M671L mice compared to the M146L or non-transgenic littermates ($p<0.05$; Neman-Keul's post-hoc comparisons). These results indicate that mice expressing an APP mutation have impaired alternation performance at a very early age. This behavioral deficit may be caused by overexpression of mutant APP, or elevated levels of soluble human A$\beta$. Importantly, this deficit is not caused by formation of visible fibrillar A$\beta$ deposits because these are either absent or rare in 12 weeks old doubly mutant mice and even by 32 weeks, these deposits are not seen in K670N,M671L mice.

A second measurement in the "Y" maze alternation test is the total number of arm entries. This index of activity was also affected by genotype (FIG. 1B; ANOVA: $F(3,43)=3.73$, $p<0.02$). The doubly transgenic mice had increased activity compared with the single transgenic K670N,M671L, M14.6L or non-transgenic mice ($p<0.05$; Newman-Koul's post-hoc comparisons). The K670N,M671L mice were not significantly different from the other two genotypes on this measure. FIG. 1C demonstrates the rightward shift of the frequency distribution for the activity scores of doubly transgenic mice, indicating this is not the result of the a new outlying animals. Thus, as early as 12 weeks, there is a synergistic effect of PS1 and APP mutations on this behavioral measure.

These results clearly demonstrate that presenilin mutations accelerate development of the AD phenotype in K670N,MG71L mice in a synergistic manner. The data indicate that mutant presenilin affects the processing of mutant APP expressed from the K670N,M671L transgene to enhance fibrillar plaque formation and affect behavior early in the life-spans of mice. The rapid development of the AD phenotype in these mice will be advantageous in addressing mechanistic issues of amyloid toxicity, and, potentially, testing the efficacy of agents proposed to interact with select aspects of the AD phenotype.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

DEPOSIT NUMBER IN DOUBLY TRANSGENIC AND K670N, M671L MICE

| Mouse | Age | TS | CR | A$\beta$ (IHC) |
|---|---|---|---|---|
| Doubly Transgenic Mice plaque counts/section | | | | |
| F2 | 26 | 77 | 34 | 58 |
| F7 | 26 | 61 | 26 | 31 |
| G3 | 26 | 48 | 24 | 34 |
| G6 | 26 | 97 | 43 | 53 |
| C7 | 29 | 78 | 42 | 48 |
| A5 | 32 | 101 | 44 | 54 |
| K670N, M671L Mice plaque counts/section | | | | |
| H6 | 24 | 0 | 0 | 0 |
| F5 | 26 | 0 | 0 | 0 |
| E1 | 27 | 0 | 0 | 0 |
| D3 | 28 | 0 | 0 | 0 |
| C1 | 29 | 0 | 0 | 0 |

Mice ages (weeks) with plaque numbers per section counted from thioflavin S (TS), Congo Red (CR) or A$\beta$ immunohistochemistry (IHC).

REFERENCES

Ali et al., 1996. Artificial Strain-Specific Signs of Incipient Brain Amyloidosis in APP Transgenic Mice. *Neur. of Aging,* 17(2):223–234.

Andra et al., 1996, "Expression of APP in Transgenic Mice: A Comparison of Neuron-Specific Promoters", *Neur. of Aging,* 17(2)P183–190

Borchelt et al., 1996, "Familial Alzheimer's Disease-Linked Presenilin 1 Variants Elevate A-$\beta$-1-42/1-40 Ratio in Vitro and in Vivo", *Neuron,* 17:1005–1013

Burke and Olson, 1991. "Preparation of Clone Libraries in Yeast Artificial-Chromosome Vectors" in *Methods in Enzymology,* Vol. 194, Academic Press, Inc., Chap. 17, pp. 251–270.

Cai et al., 1993, "Release of Excess Amyloid $\beta$ Protein from a Mutant Amyloid $\beta$ Protein Precursor", *Science,* 259:514–516

Capecchi, 1989, "Altering the genome by homologous recombination" *Science,* 244:1288–1292.

Citron et al., 1992, "Mutation of the $\beta$-amyloid precursor protein in familial Alzheimer's disease increases $\beta$-protein production", *Nature* 360:672

Cruts et al., 1996, "The Presenilin Genes—A New Gene Family Involved in Alzheimer Disease Pathology", *Human Molecular Genetics,* 5 (Review):1449–1455.

Davies et al., 1992, "Targeted alterations in yeast artificial chromosomes for inter-species gene transfer", *Nucleic Acids Research,* 20(11):2693–2698.

Dickinson et al., 1993, "High frequency gene targeting using insertional vectors", *Human Molecular Genetics,* Vol. 2, No. 8, pp. 1299–1302.

Duff et al., 1996, "Increased amyloid-$\beta$42(43) in brains of mice expressing mutant presenilin 1", *Nature,* 383:710–713

Duff and Lincoln, 1995. "Insertion of pathogenic mutation into yeast artificial chromosome containing human APP gene and expression in ES cells", *Res. Adv. in Alzheimer's Disease*

Games et al., 1995, "Alzheimer-type neuropathology in transgenic mice overexpressing V717F $\beta$-amyloid precursor protein", *Nature,* 373:523–527

Goate et al., 1991, "Segregation of a missense mutation in the amyloid precursor protein gene with familial Alzheimer's disease", *Nature* 349:704–706

Gordon, 1989, "Transgenic Animals", *Intl. Rev. Cytol,* 115:171–229.

Greenberg, 1996, "APP Transgenesis: Approaches Toward the Development of Animal Models for Alzheimer Neuropathology", pg. 153–171

Hsiao et al., 1996, "Correlative Memory Deficits, A-β Elevation and Amyloid Plaques in Transgenic Mice", *Science*, 274:99–102

Hsiao et al., 1995, "Age-Related CNS Disorder and Early Death in Transgenic FVB/N Mice Overexpressing Alzheimer Amyloid Precursor Proteins", *Neuron*, 15:1203–1218

Huxley et al., 1991, "The human HPRT gene on a yeast artificial chromosome is functional when transferred to mouse cells by cell fusion", *Genomics*, 9:742–750.

Jakobovits et al., 1993, "Germ-line transmission and expression of a human-derived yeast artificial chromosome", *Nature*, 362:255–261

Jarrett et al., 1993, "Carboxy Terminus of β-Amyloid Protein is Critical for Seeding of Amyuloid Formation: Implications for Pathogenesis of Alzheimer's Disease", *Biochemistry*, 32:4693–4697

Lalonde and Thifault, 1994, "Absence of an Association Between Motor Coordination and Spatial Orientation in Lurcher Mutant Mice", *Behavior*, 24:497–501

Lamb et al., 1993. "Introduction and expression of the 400 kilobase precursor amyloid protein gene in transgenic mice", *Nature Genetics*, 5:22–29

Lavitrano et al, 1989, "Sperm Cells as Vectors for Introducing Foreign DNA into Eggs: Genetic Transformation of Mice" *Cell* 57:717–723

Levy-Lahad et al., 1995, "Candidate Gene for Chromosome 1 Familial Alzheimer's Disease Locus", *Science*, 269:973–977

L'Hernault and Arduengo, 1992, "Mutation of Putative Sperm Membrane Protein in *Caenorhabditis elegans* Prevents Sperm Differentiation", *J. Cell Biology*, 119(1):55–68

Lo, 1983, "Transformation by Iontophoretic Microinjection of DNA Multiple Integrations Without Tandem Insertions", *Mol. Cell. Biol* 3(10):1803–1814

Loring et al., 1996, "Rational Design of Animal Model for Alzheimer's Disease: Introd. of Mult. Human Genomic Transgenes to Reproduce AD Pathology in Rodent", *Neur. of Aging*, 17(2):173–182

Mann et al., 1996, "Amyloid a Protein Deposition in Chrom. 14-linked Alzheimer's Disease", *Annals Neurol*, 40:149–156

Malherbe et al., 1996, "Lack of β-Amyloidosis in Transgenic Mice Expressing Low Levels of Aamilial Alzheimer's Disease Missence Mutations", 17(2): 205–214

Mucke et al., 1994, "Synaptotrophic effects of human amyloid β protein precursors in cortex of transgenic mice", *Brain Res.*, 666:151–167

Neve et al., 1996, "Transgenic Mice expressing APP-C100 in the Brain", *Neuro. of Aging*, 17(2):191–203

Pearson and Choi, 1993, "Expression of the human β-amyloid precursor protein gene from a yeast artificial chromosome in transgenic mice". *Proc. Natl. Scad. Sci. USA*, 90:10578–10582

Reaume et al., 1996, Enhanced amyuloidogenic processing of the β-amyloid precursor protein in gene-targeted mice bearing the Swedish familial Alzheimer's disease mutations and a "humanized" Aβ sequence. *J. Biol. Chem.* 271(38):23380–23388.

Rothstein, 1991, "Targeting, disruption, replacement, and allele rescue: integrative DNA transformation in yeast" in *Methods in Enzymology*, (Academic Press) Chap. 19, 194:281–301.

Schedl et al., 1993, "A yeast artificial chromosome covering the tyrosinase gene confers copy number-dependent expression in transgenic mice", *Nature*, Vol. 362, pp. 258–261.

Scheuner et al., 1996, "Secreted amyloid β-protein similar to that in the senile plaques of Alzheimer's Disease is increased in vivo by the presenilin 1 and 2 and APP mutations linked to familial Alzheimer's Disease", *Nature Medicine*, 2(8):864–870.

Sherrington et al., 1996, "Cloning of a gene bearing missense mutations in early-onset familial Alzheimer's disease", *Nature*, 375:754–760

Strauss et al., 1993, "Germ line transmission of a yeast artificial chromosome spanning the murine $\alpha_1$ (I) collagen locus", *Science*, 259:1904–1907.

Suzuki et al., 1994, "Increased Percentage of Long Amyloid β Protein Secreted by Familial Amyloid β Protein Precursor ($\beta APP_{717}$) Mutants", *Science*, 264:1336–1340

Thompson et al, 1989, "Germ Line Transmission and Expression of a Corrected HPRT Gene Produced by Gene Targeting in Embryonic Stem Cells", *Cell* 56:313–321

Van der Putten et al, 1985, "Efficient insertion of genes into the mouse germ line via retroviral vectors", PNAS USA 82:6148–6152.

What is claimed is:

1. A transgenic mouse with enhanced Alzheimer's Disease related amyloid accumulation in its brain produced by:
    producing an $F_1$ generation mouse by crossing a first transgenic mouse whose genome comprises at least one transgene comprising a DNA sequence encoding mutant presenilin M146L operably linked to a promoter with a second transgenic mouse whose genome comprises at least one transgene comprising a DNA sequence encoding APP K670N,M671L operably linked to a promoter, wherein the first transgenic mouse expresses the DNA sequence encoding the mutant presenilin and wherein the second transgenic mouse expresses the DNA sequence encoding the APP; and
    selecting from the offspring of the cross, those transgenic mice whose genome comprises at least one DNA sequence encoding mutant presenilin M146L operably linked to a promoter and at least one transgene comprising a DNA sequence encoding APP K670N,M671L operably linked to a promoter, and identifying an $F_1$ mouse which express both transgenes such that the $F_1$ mouse develops accelerated deposition of Aβ in its brain as compared to non-transgenic mice or either parental mouse.

2. The mouse as set forth in claim 1, wherein the first transgenic mouse is homozygous for the mutant presenilin transgene.

3. A transgenic mouse with accelerated Alzheimer's Disease related pathology whose genome comprises at least one least one transgene comprising a DNA sequence encoding mutant presenilin M146L operably linked to a promoter and at least one transgene comprising a DNA sequence encoding APP K670N,M671L operably linked to a promoter, wherein the mouse expresses the transgenes such that the mouse develops accelerated deposition of Aβ in their brains as compared to non-transgenic mice or transgenic mice expressing either transgene.

4. The mouse as set forth in claim 3, wherein the first transgenic mouse is homozygous for the mutant presenilin transgene.

5. A transgenic mouse with accelerated Alzheimer's Disease related pathology whose genome comprises at least one least one transgene comprising a DNA sequence encoding mutant presenilin M146L operably linked to a promoter and at least one transgene comprising a DNA sequence encoding APP K670N,M671L operably linked to a promoter, wherein the mouse expresses the transgenes such that the mouse develops accelerated deposition of Aβ in its brain within six months of birth as compared to non-transgenic mice or transgenic mice expressing either transgene.

6. The mouse as set forth in claim 5, wherein the first transgenic mouse is homozygous for the mutant presenilin transgene.

7. A transgenic mouse with accelerated Alzheimer's Disease related pathology whose genome comprises at least one least one transgene comprising a DNA sequence encoding mutant presenilin operably linked to a promoter and at least one transgene comprising a DNA sequence encoding APP K670N,M671L operably linked to a promoter, wherein the mouse expresses the transgenes such that the accelerated pathology develop accelerated deposition of Aβ in its brain as compared to non-transgenic mice or mice expressing either transgene.

8. A transgenic mouse with elevated levels of amyloidogenic Aβ (Aβ42(43)) as a pathology for Alzheimer's Disease whose genome comprises at least one least one transgene comprising a DNA sequence encoding mutant presenilin operably linked to a promoter and at least one transgene comprising a DNA sequence encoding APP K670N,M671L operably linked to a promoter, wherein the mouse expresses the transgenes such that the mouse develops accelerated deposition of Aβ (Aβ42(43)) in its brain as compared to non-transgenic mice or transgenic mice expressing either transgene.

9. A transgenic mouse with elevated levels of amyloidogenic Aβ (Aβ42(43)) as a pathology for Alzheimer's Disease whose genome comprises at least one least one transgene comprising a DNA sequence encoding mutant presenilin M146L operably linked to a promoter and at least one transgene comprising a DNA sequence encoding APP K670N,M671L operably linked to a promoter, wherein the mouse expresses the transgenes such that an elevated level of Aβ (Aβ42(43)) protein deposits in it's brain as compared to non-transgenic mice or transgenic mice expressing either transgene.

10. A method of screening for two expressible transgenes, the method comprising:

producing an $F_1$ generation mouse by crossing a first transgenic mouse whose genome comprises at least one transgene comprising a DNA sequence encoding mutant presenilin operably linked to a promoter with a second transgenic mouse whose genome comprises at least one transgene comprising a DNA sequence encoding APP K670N,M671L operably linked to a promoter, wherein the first transgenic mouse expresses the DNA sequence encoding the mutant presenilin and wherein the second transgenic mouse expresses the DNA sequence encoding the APP; and selecting from the offspring of the cross, those transgenic mice whose genome comprises at least one DNA sequence encoding mutant presenilin operably linked to a promoter and at least one transgene comprising a DNA sequence encoding APP K670N,M671L operably linked to a promoter, and identifying an $F_1$ mouse which express both transgenes such that the $F_1$ mouse develops accelerated deposition of Aβ in its brain as compared to non-transgenic mice or either parental mouse.

11. A method for preparing a transgenic mouse with elevated levels of amyloidogenic Aβ (Aβ42(43)) as a pathology for Alzheimer's Disease the method comprising:

producing an $F_1$ generation mouse by crossing a first transgenic mouse whose genome comprises at least one transgene comprising a DNA sequence encoding mutant presenilin operably linked to a promoter with a second transgenic mouse whose genome comprises at least one transgene comprising a DNA sequence encoding APP K670N,M671L operably linked to a promoter, wherein the first transgenic mouse expresses the DNA sequence encoding the mutant presenilin and wherein the second transgenic mouse expresses the DNA sequence encoding the APP; and selecting from the offspring of the cross, those transgenic mice whose genome comprises at least one DNA sequence encoding mutant presenilin operably linked to a promoter and at least one transgene comprising a DNA sequence encoding APP K670N,M671L operably linked to a promoter, and identifying an $F_1$ mouse which express both transgenes such that the $F_1$ mouse develops accelerated deposition of Aβ (Aβ42(43)) in their brains as compared to non-transgenic mice or either parental mouse.

12. The method as set forth in claim 11, wherein the mutant presenilin is M146L.

13. A method of preparing a transgenic mouse with enhanced Alzheimer's Disease related amyloid pathology, the method comprising:

producing an $F_1$ generation mouse by crossing a first transgenic mouse whose genome comprises at least one transgene comprising a DNA sequence encoding mutant presenilin M146L operably linked to a promoter with a second transgenic mouse whose genome comprises at least one transgene comprising a DNA sequence encoding APP K670N,M671L operably linked to a promoter, wherein the first transgenic mouse expresses the DNA sequence encoding the mutant presenilin and wherein the second transgenic mouse expresses the DNA sequence encoding the APP; and selecting from the offspring of the cross, those transgenic mice whose genome comprises at least one DNA sequence encoding mutant presenilin M146L operably linked to a promoter and at least one transgene comprising a DNA sequence encoding APP K670N,M671L operably linked to a promoter, and identifying an $F_1$ mouse which express both transgenes such that the $F_1$ mouse develops accelerated deposition of AD in its brain as compared to non-transgenic mice or either parental mouse.

14. The method as set forth in claim 13, wherein the first transgenic mouse is homozygous for the mutant presenilin transgene.

* * * * *